United States Patent [19]

Enkoji et al.

[11] 4,089,821
[45] May 16, 1978

[54] SYNTHESIS OF PEPTIDE AMIDES

[75] Inventors: Takashi Enkoji, Park Forest; Martin O. Skibbe, Kankakee, both of Ill.

[73] Assignee: Armour Pharmaceutical Company, Phoenix, Ariz.

[21] Appl. No.: 672,459

[22] Filed: Mar. 31, 1976

[51] Int. Cl.² ............... C08L 37/00; C07C 103/52; A61K 37/00
[52] U.S. Cl. ............... 260/8; 260/112.5 R; 424/177
[58] Field of Search ............ 260/112.5 R, 8

[56] References Cited

U.S. PATENT DOCUMENTS

| | | | |
|---|---|---|---|
| 3,388,112 | 6/1968 | Geiger et al. | 260/112.5 R |
| 3,483,291 | 12/1969 | Vogel et al. | 260/112.5 R |
| 3,651,039 | 3/1972 | Fujino et al. | 260/112.5 R |
| 3,749,704 | 7/1973 | Geiger et al. | 260/112.5 R |
| 3,759,891 | 9/1973 | Otsuka et al. | 260/112.5 R |
| 3,761,459 | 9/1973 | Pless et al. | 260/112.5 R |
| 3,761,461 | 9/1973 | Pless et al. | 260/112.5 R |
| 4,001,199 | 1/1977 | Fujino et al. | 260/112.5 R |

OTHER PUBLICATIONS

R. L. Colescott, et al.; Chem. Abst. 85, p. 177917k.
Pietta et al., J. Org. Chem., 39, 44-48 (1974).

*Primary Examiner*—Delbert R. Phillips
*Attorney, Agent, or Firm*—Richard R. Mybeck; Carl C. Batz

[57] ABSTRACT

Peptide amides having biological activity and resin peptide amides useful in the preparation of peptides having biological activity, particularly such peptides containing the structure

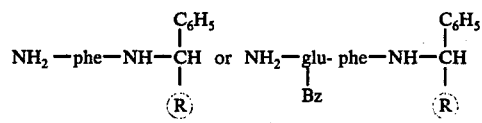

in which Ⓡ is divinylbenzene crosslinked polystyrene and Bz is benzyl, p-methoxybenzyl, p-chlorobenzyl, p-nitrobenzyl, or benzhydryl, and in which phe and glu are residues of the amino acids phenylalanine and glutamic acid; and processes for preparing such peptide amides.

Resin peptide amides are disclosed which contain amino acid chains identical with the amino acid chains of natural peptides having biological activity. Other resin peptide amides are disclosed which contain amino acid chains in which the amino acid residues differ in kind or sequence from amino acid chains of natural biologically active peptides but from which peptides having biological activity may be derived.

25 Claims, No Drawings

SYNTHESIS OF PEPTIDE AMIDES

This invention relates to the synthesis of peptides and particularly resin peptides which are useful in the production of biologically active products such as adrenocorticotropic hormones.

BACKGROUND

It has long been known that certain biologically active substances can be obtained from the glands of animals and the substances so obtained utilized in the treatment of deficiencies of the human body. One such substance is the adrenocorticotropic hormone, commonly called ACTH, which for many years has been obtained from the pituitary glands of animals, particularly porcine and bovine pituitary glands.

For many years the art has eargerly awaited the discovery of more practical methods and compounds which enable the commercial synthesis of such peptides from other than natural sources. One such synthesis is set forth by Colescott, Kaiser, Bossinger and Cook in the U.S. Pat. No. 3,915,949 dated Oct. 28, 1975.

The solid phase synthesis set forth in that patent utilizes insoluble polystyrene resin which is prepared by catalytic polymerization of styrene and divinyl benzene and this is chloromethylated using chloromethyl ether and stannic chloride catalyst.

SUMMARY

We have discovered that by utilizing a benzhydrylamine resin, it is possible to obtain peptides of greater potency and effectiveness with reduction of "peptide loss" during synthesis. The use of such a resin results in novel intermediate compounds and processes which contribute substantial practical improvement in the manufacture of products having hormonal activity.

DESCRIPTION

In general we use a solid phase synthesis utilizing a benzhydrylamine resin. This resin is prepared from resin beads obtained from the catalytic polymerization of styrene and divinyl benzene. These resin beads are subjected to a series of chemical reactions described by Pietta, et al. (P. G. Pietta, P. F. Cavallo, K. Takahashi, and G. R. Marshall, *J. Org. Chem.*, 39,44 [1974]), and this results in a resin which contains benzhydrylamine groups, and which we call BHA resin. This resin may be represented by the structure:

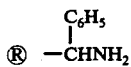

in which ®is the divinyl benzene crosslinked polystyrene portion of the resin and $C_6H_5$ is a benzene ring.

This resin is now available on the market from chemical supply houses.

Resin Peptide Synthesis

The amino acids are added one at a time to the insoluble BHA resin until the total desired peptide sequence has been built up on the resin. The α-amino groups of the amino acid derivatives are protected during addition to the resin by an acid labile protecting group which may be tertiary-butyloxycarbonyl (BOC), or amyloxycarbonyl (AMOC) or biphenyloxycarbonyl (BPOC). Some amino acids contain functional groups other than α-carboxyl and α-amino groups which may react with the amino acid derivatives being added causing the formation of undesirable by-products. These groups may be protected by blocking groups as follows:

The hydroxyl function of serine is protected by a benzyl or benzyl derivative group such as 4-methoxybenzyl, 4-methylbenzyl, 3, 4-dimethylbenzyl, 4-nitrobenzyl, benzhydryl or an equivalent thereof. We use the term Bz to represent this benzyl or benzyl derivative group.

The hydroxyl function of tyrosine may be unprotected or may be protected by a Bz group as above described or may be protected by a benzyloxycarbonyl or a benzyloxycarbonyl derivative such as 2-chlorobenzyloxycarbonyl or a 2-bromobenzyloxycarbonyl group or the equivalent thereof. We use the term Y to represent either no protective group (in which Y is H), a Bz group, a benzyloxycarbonyl group or a benzyloxycarbonyl derivative group.

The guanidino function of arginine may be protected by a nitro group, a tosyl group or an equivalent thereof. We use the character T to represent either a nitro group or a tosyl group or the equivalent thereof.

Where lysine is attached we prefer to use as the ε-amino protection agent 2-chlorobenzyloxycarbonyl but may also use benzyloxycarbonyl (Z), 2-bromobenzyloxycarbonyl, or 2, 4-dichlorobenzyloxycarbonyl. We use the symbol V to represent such a group.

The amide function of asparagine or of glutamine may be unprotected or may be protected by a xanthydryl or a benzhydryl group. We use the character P' to designate hydrogen or such a group.

The protective group preferred on the imidazole nitrogen of histidine is the benzyloxycarbonyl group but may be tosyl, dinitrophenyl, benzyl, benzyl derivative or no protective group. We use the symbol W to indicate either no protective group or any of the named derivatives.

The α-carboxylic acid group or glutamic acid is protected by a Bz group.

A coupling agent (CA) such as dicyclohexylcarbodiimide (DCC) or other coupling agent which forms peptide bonds such as diimides, azides or anhydrides or active esters may be utilized in the coupling reactions. In the attachment of asparagine or glutamine the DCC coupling agent should not be used unless the asparagine or glutamine has a suitable protecting group such a benzhydryl or xanthydryl, attached thereto. Without such protection DCC creates a side reaction which destroys some of the asparagine or glutamine. Alternately, asparagine or glutamine can be coupled, when unprotected, as an active ester.

The addition of each amino acid derivative is followed by a deblocking or deprotection step in which an acid such as trifluoroacetic acid is used to remove the group protecting the α-amino group. The deprotected amine group, after neutralization and washing, is then ready for the addition of the next amino acid derivative.

According to accepted practice the amino acid positions in peptides are numbered beginning with position number 1 at the amino terminus and ending with the carboxyl terminus, which for ACTH would begin with position number 1 for serine and end with position number 39 at phenylalanine. We will follow this same numbering system in the description of the present synthesis.

With respect to ACTH, the first coupling of an amino acid moiety will be at position number 39 and the last will be at position number 1. Likewise, the first cycle for coupling an amino acid moiety at position number 39 and will be called cycle 39, and the last cycle for coupling an amino acid moiety will be at position number 1 and will be called cycle number 1.

There are two known sequences of amino acids for the hormone ACTH. One of these may be called the sequence A given as follows:

ser-tyr-ser-met-glu-his-phe-arg-trp-gly-lys-pro-
 1   2   3   4   5   6   7   8   9  10  11  12
val-gly-lys-lys-arg-arg-pro-val-lys-val-tyr-
 13  14  15  16  17  18  19  20  21  22  23
pro-asp-ala-gly-glu-asp-gln-ser-ala-glu-ala
 24  25  26  27  28  29  30  31  32  33  34
phe-pro-leu-glu-phe
 35  36  37  38  39 and the other, which we call sequence B, given as follows:

ser-tyr-ser-met-glu-his-phe-arg-trp-gly-lys-pro-
 1   2   3   4   5   6   7   8   9  10  11  12
val-gly-lys-lys-arg-arg-pro-val-lys-val-tyr-
 13  14  15  16  17  18  19  20  21  22  23
pro-asn-gly-ala-glu-asp-glu-ser-ala-glu-ala-
 24  25  26  27  28  29  30  31  32  33  34
phe-pro-leu-glu-phe-
 35  36  37  38  39

For each coupling reaction we may use the selected amino acid along with protective groups suitably in the form of a combined derivative. Such derivatives may be purchased or prepared by known procedures. Preferred reactants for use in each of the 39 cycles are listed in Table No. 1 as follows:

TABLE NO. 1

| Cycle No. | |
|---|---|
| 39 | BOC-L-phenylalanine |
| 38 | BOC-L-glutamic acid γ-benzyl ester |
| 37 | BOC-L-leucine |
| 36 | BOC-L-proline |
| 35 | BOC-L-phenylalanine |
| 34 | BOC-L-alanine |
| 33 | BOC-L-glutamic acid γ-benzyl ester |
| 32 | BOC-L-alanine |
| 31 | BOC-O-benzyl-L-serine |
| 30 | BOC-L-glutamine p-nitrophenyl ester |
| 29 | BOC-L-aspartic acid β-benzyl ester |
| 28 | BOC-L-glutamic acid γ-benzyl ester |
| 27 | BOC-glycine |
| 26 | BOC-L-alanine |
| 25 | BOC-L-aspartic acid β-benzyl ester |
| 24 | BOC-L-proline |
| 23 | BOC-O-(2-bromobenzyloxycarbonyl)-L-tyrosine |
| 22 | BOC-L-valine |
| 21 | BOC-ε-(2-chlorobenzyloxycarbonyl)-L-lysine |
| 20 | BOC-L-valine |
| 19 | BOC-L-proline |
| 18 | BOC-N$^g$-tosyl-L-arginine |
| 17 | BOC-N$^g$-tosyl-L-arginine |
| 16 | BOC-ε-(2-chlorobenzyloxycarbonyl)-L-lysine |
| 15 | BOC-ε-(2-chlorobenzyloxycarbonyl)-L-lysine |
| 14 | BOC-glycine |
| 13 | BOC-L-valine |
| 12 | BOC-L-proline |
| 11 | BOC-ε-(2-chlorobenzyloxycarbonyl)-L-lysine |
| 10 | BOC-glycine |
| 9 | BOC-L-tryptophan |
| 8 | BOC-N$^g$-tosyl-L-arginine |
| 7 | BOC-L-phenylalanine |
| 6 | BOC-N(im)-benzyloxycarbonyl-L-histidine |
| 5 | BOC-L-glutamic acid γ-benzyl ester |
| 4 | BOC-L-methionine |
| 3 | BOC-O-benzyl-L-serine |
| 2 | BOC-O-(2-bromobenzyloxycarbonyl)-L-tyrosine |
| 1 | BOC-O-benzyl-L-serine |

Each of the amino acid derivatives mentioned in Table No. 1 is commercially available from suppliers and may be utilized in preparing compounds according to the A sequence above referred to.

In Table No. 2 there are listed reactants recommended for use in each of the 39 cycles for preparing compounds according to the B sequence. These reactants listed in Table No. 2 are also commercially available.

TABLE NO. 2

| Cycle No. | |
|---|---|
| 39 | BOC-L-phenylalanine |
| 38 | BOC-L-glutamic acid γ-benzyl ester |
| 37 | BOC-L-leucine |
| 36 | BOC-L-proline |
| 35 | BOC-L-phenylalanine |
| 34 | BOC-L-alanine |
| 33 | BOC-L-glutamic acid γ-benzyl ester |
| 32 | BOC-L-alanine |
| 31 | BOC-O-benzyl-L-serine |
| 30 | BOC-L-glutamic acid γ-benzyl ester |
| 29 | BOC-L-asparic acid β-benzyl ester |
| 28 | BOC-L-glutamic acid γ-benzyl ester |
| 27 | BOC-L-alanine |
| 26 | BOC-glycine |
| 25 | BOC-L-asparagine p-nitrophenyl ester |
| 24 | BOC-L-proline |
| 23 | BOC-O-(2-bromobenzyloxycarbonyl)-L-tyrosine |
| 22 | BOC-L-valine |
| 21 | BOC-ε-(2-chlorobenzyloxycarbonyl)-L-lysine |
| 20 | BOC-L-valine |
| 19 | BOC-L-proline |
| 18 | BOC-N$^g$-tosyl-L-arginine |
| 17 | BOC-N$^g$-tosyl-L-arginine |
| 16 | BOC-ε-(2-chlorobenzyloxycarbonyl)-L-lysine |
| 15 | BOC-ε-(2-chlorobenzyloxycarbonyl)-L-lysine |
| 14 | BOC-glycine |
| 13 | BOC-L-valine |
| 12 | BOC-L-proline |
| 11 | BOC-ε-(2-chlorobenzyloxycarbonyl)-L-lysine |
| 10 | BOC-glycine |
| 9 | BOC-L-tryptophan |
| 8 | BOC-N$^g$-tosyl-L-arginine |
| 7 | BOC-L-phenylalanine |
| 6 | BOC-N(im)-benzyloxycarbonyl-L-histidine |
| 5 | BOC-L-glutamic acid γ-benzyl ester |
| 4 | BOC-L-methionine |
| 3 | BOC-O-benzyl-L-serine |
| 2 | BOC-O-(2-bromobenzyloxycarbonyl)-L-tyrosine |
| 1 | BOC-O-benzyl-L-serine |

Compounds made according to the A sequence and also compounds made according to the B sequence may be prepared by following through the reaction cycles up to and including cycle 2 which is the addition of tyrosine. In the case of either sequence, the resin peptide is coupled in cycle No. 1 with BOC-O-benzyl-L-serine, as above described or with BOC-O-benzyl-D-serine, BOC-L-alanine, BOC-β-alanine, BOC-D-alanine or BOC-glycine. Use of any of the named reactants at cycle 1 results in a compound having adrenocorticotropic hormone activity.

In the following descriptive matter, more explicit directions will be given for preparing adrenocorticotropic hormone compounds according to sequence A and also according to sequence B, utilizing the reactants listed in Tables 1 and 2.

PREPARATION OF SEQUENCE A

Cycle 39

Coupling of BOC-L-phenylalanine to BHA resin

The reaction vessel used in all steps of the resin peptide synthesis may be a glass vessel equipped with inlet ports at the top for addition of materials and a sintered glass disc at the bottom for removal of soluble excess reactants, by-products and solvents by filtration. The filtration can be performed either by vacuum or pressure. The contents of the vessel can be mixed by mechanical shaking of the entire vessel or by a mechanical stirrer.

In Cycle 39, the BHA resin is placed in the reaction vessel and washed with methylene chloride, chloroform, dimethylformamide or any suitable organic solvent or any combination of these solvents. The washed BHA resin is resuspended in the solvent selected, and BOC-L-phenylalanine in an amount of 1 to 6 equivalents per equivalent of BHA resin used is added. After mixing for 5 to 10 minutes, a coupling agent (CA) such as dicyclohexylcarbodiimide (DCC) may be added in the amount of 0.5 to 2.0 equivalents per equivalent of BOC-L-phenylalanine used.

The BOC-L-phenylalanine may be coupled in the absence of a coupling agent if its active ester, azide, or the symmetrical or mixed anhydride is used. The activated ester may be 2-nitrophenyl, 4-nitrophenyl, pentafluorophenyl, pentachlorophenyl, N-hydroxysuccinimide ester or any other such active ester. The active esters may be used in amounts of 1 to 10 equivalents per free amine equivalent of BHA resin.

The reaction mixture consisting of BHA resin, solvent, BOC-L-phenylalanine and coupling agent or the reaction mixture of BHA resin, solvent and BOC-L-phenylalanine active ester is mixed until the reaction is complete as indicated by a ninhydrin test (E. Kaiser et al., *Anal. Biochem.*, 34,595–8 [1970]) on a test sample. When the coupling reaction is complete, the BOC-L-phenylalanine resin may be washed with a solvent such as methylene chloride, chloroform, methanol, benzene, dimethylformamide, or acetic acid. The amount of wash solvent may be 2 to 20 ml. of solvent for each gram of BHA resin used initially.

The coupling reactions to produce the BOC-L-phenylalanine resin may be illustrated by the following chemical equations.

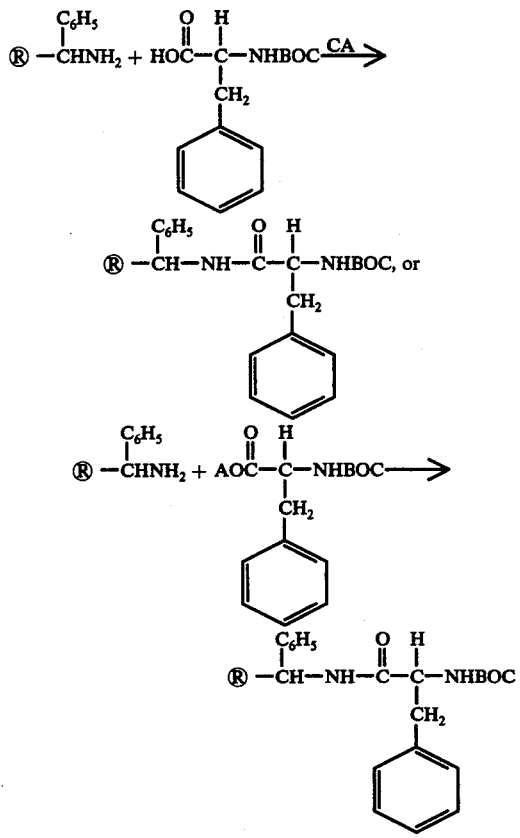

in which A represents 2-nitrophenyl, 4-nitrophenyl, pentafluorophenyl, pentachlorophenyl, succinimide or any such suitable activating group.

Deprotection of BOC-L-phenylalanine Resin

The BOC-L-phenylalanine resin from above may be deprotected by mixing with trifluoroacetic acid either alone or in combination with methylene chloride, chloroform, benzene, toluene or any other such solvent. The amount of TFA in the solvent can vary from 100% to 10% and the TFA-solvent mixture may vary from 2 to 20 ml. per gram of BHA resin used initially. The reaction time may vary from 10 minutes to 4 hours, and the deprotection step is terminated by filtration to remove the TFA-solvent mixture. The residual TFA may be removed from the L-phenylalanine resin by washing with methylene chloride or chloroform, followed by methanol or ethanol and again with methylene chloride or chloroform. The L-phenylalanine resin, which is in the trifluoroacetate salt form at this stage may be neutralized with a solution of 5 to 30% triethylamine in methylene chloride or chloroform. The amount of triethylamine solution may be 3 to 20 ml. per gram of BHA resin. (Other amines of sufficient basic strength may be used in place of triethylamine.) The deprotection reaction may be illustrated by the following equation:

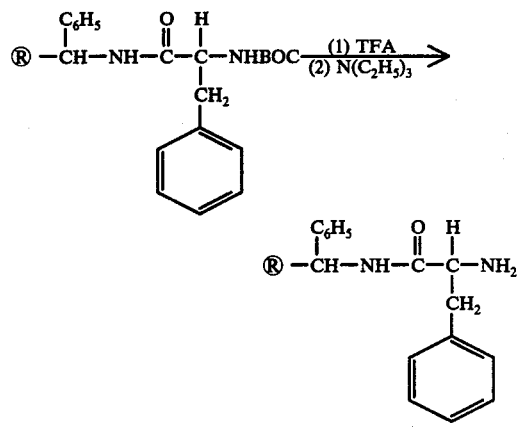

The product of the reaction according to the above formula may be represented, in abbreviated form as follows:

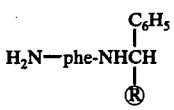

Cycle 38

The phenylalanine BHA resin obtained from Cycle 39 may be resuspended in a coupling solvent and BOC-L-glutamic acid γ-benzyl ester added. After mixing for 5 to 10 minutes, the coupling agent (CA) may be added. When the reaction is completed, as indicated by the ninhydrin test, the soluble reaction solution may be removed from the BOC-γ-benzylglutamylphenylalanyl BHA resin by filtration. The resin peptide may be washed with solvents. The amounts of reactants, solvents and reaction conditions may be essentially the same as those described for Cycle 39. The BOC group may be removed from the resin peptide by the deprotection method described in Cycle 39. The reactions of Cycle 38 may be illustrated by the following equations:

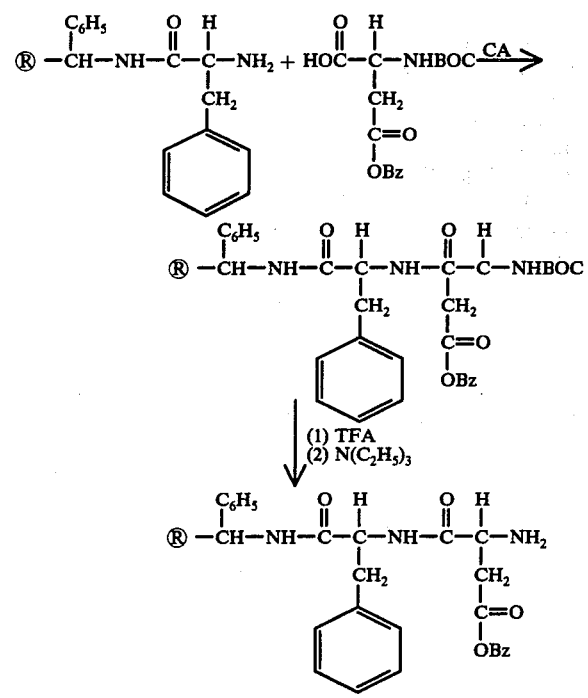

For convenience, we may represent this resulting resin peptide using abbreviated nomenclature as follows:

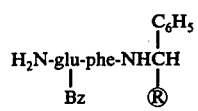

Cycle 37

In Cycle 37, the coupling and deprotection reactions may be performed in the same manner as in Cycle 38 except that BOC-L-leucine is used in place of BOC-L-glutamic acid γ-benzyl ester. These reactions may be illustrated by the following equation.

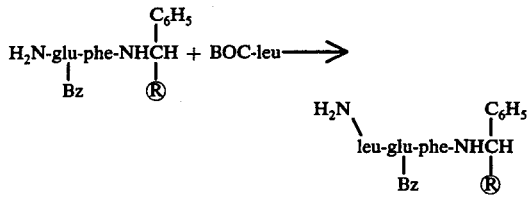

Cycles 36–31

In each of Cycles 36–31, the coupling and deprotection reactions may be conducted in the proper sequence using the methods and conditions described in Cycle 39 using BOC-L-proline in Cycle 36, BOC-L-phenylalanine in Cycle 35, BOC-L-alanine in Cycle 34, BOC-L-glutamic acid γ-benzyl ester in Cycle 33, BOC-L-alanine in Cycle 32, BOC-O-benzyl-L-serine in Cycle 31. The resin peptide resulting from the completion of Cycle 31 may be written:

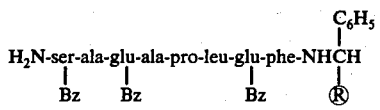

Cycle 30

In Cycle 30, the coupling reaction may be performed using an active ester derivative of BOC-L-glutamine in order to avoid a known side reaction which occurs with the DCC couplings of BOC-L-glutamine and BOC-L-asparagine. The active ester in the amount of 2 to 10 equivalents is added per amine equivalent of BHA resin in dimethylformamide in amounts of 2 to 20 ml. of solvent per gram of BHA resin used initially. Reaction times may vary from 1 to 72 hours. The protected resin peptide is separated from the reaction mixture by filtration after completion of reaction as indicated by a ninhydrin test. The active esters employed may be 2-nitrophenyl, 4-nitrophenyl, pentafluorophenyl, pentachlorophenyl, N-hydroxysuccinimido or any other suitable activating group. Using AE to designate the active ester portion, the coupling reaction may be written:

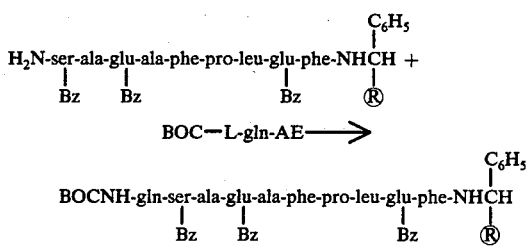

The deprotection reaction to remove the BOC group is performed as in Cycle 32.

Cycles 29–25

In each of Cycles 29–25, the coupling and deprotection reactions may be conducted in the proper sequence using the methods and conditions described in Cycle 39. The protected amino acid derivatives used are BOC-L-aspartic acid β-benzyl ester in Cycle 29, BOC-L-glutamic acid γ-benzyl ester in Cycle 28, BOC-glycine in Cycle 27, BOC-L-alanine in Cycle 26, BOC-L-aspartic acid β-benzyl ester in Cycle 25. The resin peptide resulting from the completion of Cycle 25 may be written:

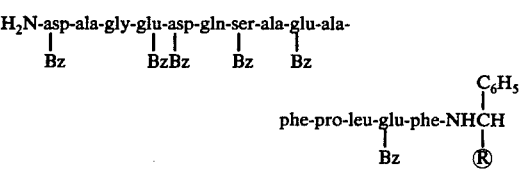

Cycles 24–2

In each of Cycles 24–2, the coupling and deprotection reactions may be conducted in the proper sequence using the methods and conditions described in Cycle 39. The protected amino acid derivatives for each cycle are listed in Table II. The resin peptide resulting from the completion of Cycle 2 may be written:

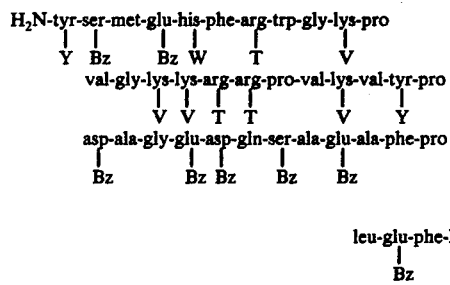

Cycle 1

In Cycle 1, the coupling and deprotection reactions may be performed in the same manner as in Cycle 39, except that BOC-O-benzyl-L-serine, BOC-O-benzyl-D-serine, BOC-L-alanine, BOC-D-alanine, BOC-β-alanine or BOC-glycine may be used. The resin peptide resulting from Cycle 1 may be written:

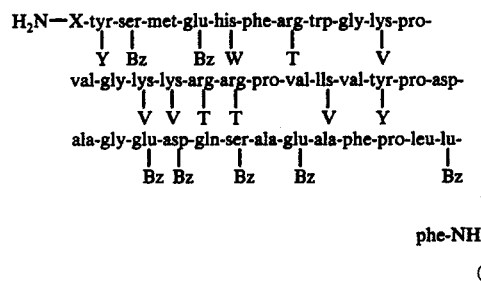

in which X is

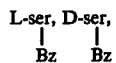

L-ala, D-ala, B-ala or gly.

PREPARATION OF SEQUENCE B

Cycles 39–31

The same reaction vessel, reaction conditions and reactants may be used in this Sequence for cycles 39 to 31 as above described in connection with Sequence A and the resin peptide so obtained after the completion of cycle 31 is identical so that obtained in Sequence A.

Cycles 30–26

In each of cycles 30 to 26 the coupling and deprotection reactions may be conducted using the reactants set forth in Table No. 2 for use at positions 30 to 26 and using the methods and conditions described for cycle 39 of Sequence A. The resin peptide so obtained at the completion of cycle 30 may be written:

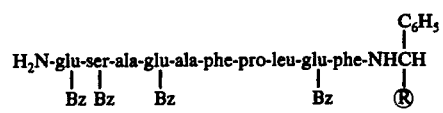

The resin peptide so obtained at the completion of cycle 26 may be written:

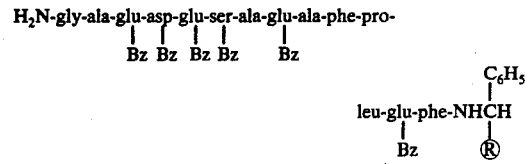

Cycle 25

Since the coupling of asparagine using the coupling agent DCC is known to produce a side reaction we prefer to avoid this by using an active ester derivative of BOC-L-asparagine. Otherwise the procedures at cycle 25 may be the same as those described for cycle 30 in Sequence A. The resin peptide resulting from cycle 25 may be written:

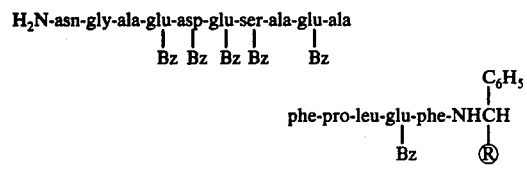

Cycles 24–2

In each of Cycles 24–2, the coupling and deprotection reactions may be conducted using the reactants for these cycles set forth in Table No. 2 and using the methods and conditions described in Cycle 39 of Sequence A. The protected amino acid derivatives for each cycle are listed in Table No. 2. The resin peptide resulting from completion of Cycle 2 may be written:

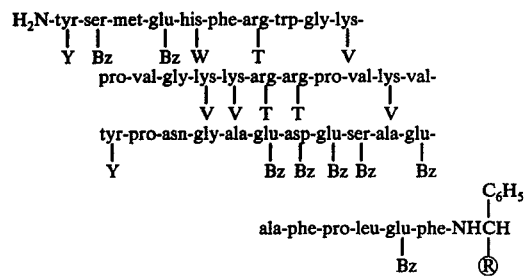

Cycle 1

In Cycle 1, the coupling and deprotection reactions may be performed in the same manner as in Cycle 39, Sequence A, except that BOC-O-Benzyl-L-serine, BOC-O-benzyl-D-serine, BOC-L-alanine, BOC-β-alanine, BOC-D-alanine or BOC-glycine may be used. The resin peptide resulting from Cycle 1 may be written:

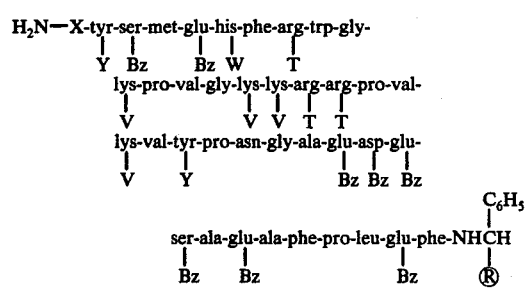

where X represents O-benzyl-L-serine, O-benzyl-D-serine, L-alanine, D-alanine, β-alanine or glycine.

Resin Peptide Cleavage

The protective groups may be cleaved from the resin peptides resulting from Cycle 1 in either Sequence A or Sequence B by treatment with liquid hydrogen fluoride (HF). The HF cleavage reaction may be performed by treating a mixture of the resin peptide and anisole (0.5 to 5 ml. for each gram of resin peptide) with liquid HF (2 to 20 ml. for each gram of resin peptide) for 0.5 to 20 hours at −20° to +15° C. The HF treatment also removes the other protective groups described previously and listed in Table No. 1.

After the reaction period, the excess HF may be removed by vacuum distillation, and the resulting mixture of peptide and resin beads may be washed with ethyl acetate or any other suitable solvent to remove anisole and residual HF. The peptides may be separated from the resin beads by extractive filtration with aqueous acetic acid. The extracts may be frozen and lyophilized to obtain the crude peptides.

For Sequence A the resulting compound after cleavage may be written:

X-tyr-ser-met-glu-his-phe-arg-trp-gly-lys-pro-val-
gly-lys-lys-arg-arg-pro-val-lys-val-try-pro-asp-ala-
gly-glu-asp-gln-ser-ala-glu-ala-phe-pro-leu-glu-phe where X is L-serine, D-serin, L-alanine, D-alanine, β-alanine or glycine. The terminal phenylalanine is understood to be an amide.

For Sequence B the resulting compound after cleavage may be written:

X-tyr-ser-met-glu-his-phe-arg-trp-gly-lys-pro-val-
gly-lys-lys-arg-arg-pro-val-lys-val-tyr-pro-asn-gly-
ala-glu-asp-glu-ser-ala-glu-ala-phe-pro-leu-glu-phe where X is L-serine, D-serine, L-alanine, D-alanine, β-alanine or glycine. The terminal phenylalanine is understood to be an amide.

Purification of Crude Amides of Human ACTH

The crude peptides may be purified by a combination of ion-exchange and gel filtration chromatography methods according to procedures known to the art. The final purified products may be obtained from solution by freeze-drying as amorphous white solids which exhibit significant adrenocortiocotropic activity when assayed by standard methods.

EXAMPLE 1

Cycle 39

A 4.65 g. (0.002 mole) quantity of BHA resin was placed in a glass reaction vessel of a peptide synthesizer. A 40 ml. volume of methylene chloride was added and after 10 minutes of mixing, 1.06 g. (0.004 mole) of BOC-L-phenylalanine was added. After 10 minutes of additional mixing, 1.8 ml. (0.004 mole) of 50% DCC in methylene chloride was added. After 2 hours of mixing, a negative ninhydrin test indicated that the coupling was complete. The resin was filtered and washed twice with 25 ml. volumes of methylene chloride, each wash being of 1 minute duration. To the washed and drained resin was added 30 ml. of 50% TFA in methylene chloride, and after 30 minutes of mixing, the resin was washed twice each for 1 minute with 30 ml. of methylene chloride, methanol and methylene chloride. Neutralization was accomplished with two 5 minute reactions with 30 ml. of 10% triethylamine in methylene chloride. The resin was washed twice with 30 ml. of methylene chloride for 1 minute.

Cycle 38

The phenylalanine resin obtained from Cycle 39 was resuspended in 30 ml. of methylene chloride and 1.35 g. (0.004 mole) of BOC-L-glutamic acid γ-benzyl ester was added. After mixing for 10 minutes, 1.8 ml. (0.004 mole) of 50% DCC in methylene chloride was added. After 2 hours of mixing, a ninhydrin test indicated that the coupling was complete. After filtration, the resin was washed twice with 25 ml. of methylene chloride, each wash being of 1 minute duration. The resin was deprotected as in Cycle 39 to obtain the resin dipeptide.

Cycle 37

To the resin dipeptide obtained from Cycle 37 was coupled 0.96 g. (0.004 mole) of BOC-L-leucine hemihydrate in the same manner as in Cycle 39. This material was deprotected with 30 ml. of 50% TFA in the same manner described in Cycle 39.

Cycles 36–31

The coupling and deprotection procedures used in these cycles were the same as in Cycle 39 except that 0.004 mole of the following amino acid derivatives was used:

| Cycle No., | Wt., g. | Amino Acid Reactant |
|---|---|---|
| 36 | 0.86 | BOC-L-proline |
| 35 | 1.06 | BOC-L-phenylalanine |
| 34 | 0.76 | BOC-L-alanine |
| 33 | 1.35 | BOC-L-glutamic acid γ-benzyl ester |
| 32 | 0.76 | BOC-L-alanine |
| 31 | 1.18 | BOC-O-benzyl-L-serine |

Cycle 30

To the resin peptide obtained from Cycle 31 was added 1.45 g. (0.004 mole) of BOC-L-glutamine p-nitrophenyl ester and 25 ml. of dimethylformamide. After 16 hours of mixing, a ninhydrin test indicated that the reaction was complete. The resin was filtered and washed with 25 ml. of dimethylformamide for 5 minutes and twice more with 25 ml. of methylene chloride for 1 minute each. This resin was deprotected as in Cycle 39.

Cycles 29–25

The coupling and deprotection procedures used in these cycles were the same as in Cycle 39 except that 0.004 mole of the following amino acid derivatives was used:

| Cycle No. | Wt., g. | Amino Acid Acid Reactant |
|---|---|---|
| 29 | 1.29 | BOC-L-aspartic acid β-benzyl ester |
| 28 | 1.35 | BOC-L-glutamic acid γ-benzyl ester |
| 27 | 0.70 | BOC-glycine |
| 26 | 0.76 | BOC-L-alanine |
| 25 | 1.29 | BOC-L-aspatic acidβ-benzyl ester |

Cycles 24–19

The coupling and deprotection procedures used in these cycles were the same as in Cycle 39 except that 0.004 mole of the following amino acid derivatives was used:

| Cycle No. | Wt., g. | Amino Acid Reactant |
|---|---|---|
| 24 | 0.86 | BOC-L-proline |
| 23 | 1.98 | BOC-O-(2-bromobenzyloxycarbonyl)-L-tyrosine |
| 22 | 0.87 | BOC-L-valine |
| 21 | 1.66 | BOC-ε-(2-chlorobenzyloxycarbonyl)-L-lysine |
| 20 | 0.87 | BOC-L-valine |
| 19 | 0.86 | BOC-L-proline |

Cycles 18–17

The coupling and deprotection procedures used in these cycles were the same as in Cycle 39, except that 0.004 mole of the following amino acid derivatives was used. The BOC-N$^g$-tosyl-L-arginine was dissolved in a mixture of 5 ml. of dimethylformamide and 25 ml. of methylene chloride before addition to the resin.

| Cycle No. | Wt., g. | Amino Acid Reactant |
|---|---|---|
| 18 | 1.70 | BOC-N$^g$-tosyl-L-arginine |
| 17 | 1.70 | BOC-N$^g$-tosyl-L-arginine |

Cycles 16–10

The coupling and deprotection procedures used in these cycles were the same as in Cycle 39 except that 0.004 mole of the following amino acid derivatives was used:

| Cycle No. | Wt., g. | Amino Acid Reactant |
|---|---|---|
| 16 | 1.66 | BOC-ε-(2-chlorobenzyloxycarbonyl)-L-lysine |
| 15 | 1.66 | BOC-ε-(2-chlorobenzyloxycarbonyl)-L-lysine |
| 14 | 0.70 | BOC-glycine |
| 13 | 0.87 | BOC-L-valine |
| 12 | 0.86 | BOC-L-proline |
| 11 | 1.66 | BOC-ε-(2-chlorobenzyloxycarbonyl)-L-lysine |
| 10 | 0.70 | BOC-glycine |

Cycles 9–8

The coupling and deprotection procedures used in these cycles were the same as in Cycle 39 except that 0.004 mole of the following amino acid derivatives was used. The BOC-L-tryptophan and BOC-N$^g$-tosyl-L-arginine were dissolved in a mixture of 5 ml. of dimethylformamide and 25 ml. of methylene chloride before addition to the resin peptide.

| Cycle No. | Wt., g. | Amino Acid Reactant |
|---|---|---|
| 9 | 1.22 | BOC-L-tryptophan |
| 8 | 1.70 | BOC-N$^g$-tosyl-L-arginine |

Cycles 7–2

The coupling and deprotection procedures used in these cycles were the same as in Cycle 39 except that 0.004 mole of the following amino acid derivatives was used:

| Cycle No. | Wt., g. | Amino Acid Reactant |
|---|---|---|
| 7 | 1.06 | BOC-L-phenylalanine |
| 6 | 1.55 | BOC-N(im)-benzyloxycarbonyl-L-histidine |
| 5 | 1.35 | BOC-L-glutamic acid γ-benzyl ester |
| 4 | 1.00 | BOC-L-methionine |
| 3 | 1.18 | BOC-O-benzyl-L-serine |
| 2 | 1.98 | BOC-O-(2-bromobenzyloxycarbonyl)-L-tyrosine |

The resin peptide from Cycle 2 was dried overnight in a vacuum oven at 50° C. to yield 13.04 g.

Cycle 1

A 3.25 g. quantity of resin peptide from Cycle 2, Example 1 was washed for 1 minute with 25 ml. of methylene chloride. To the filtered resin was added 0.30 g. (0.001 mole) of BOC-O-benzyl-L-serine and 25 ml. of methylene chloride. After mixing for 10 minutes, 0.48 ml. (0.001 mole) of 50% DCC in methylene chloride was added. After mixing for 2 hours, a ninhydrin test indicated that the reaction was complete. The resin was deprotected in the same manner described in Cycle 39, Example 1 with 25 ml. of 50% TFA in methylene chloride. This resin peptide, when neutralized and dried, weighed 3.10 g.

EXAMPLE 2

Cycle 39

A 6.00 g. (0.0026 mole) quantity of benzhydrylamine resin was placed in a glass reaction vessel of a peptide synthesizer and washed once with 40 ml. of methylene chloride for 1 minute. To the filtered resin was added a solution of 1.38 g. (0.0052 mole) of BOC-L-phenylalanine in 30 ml. of methylene chloride. After shaking for 10 minutes, 2.32 ml. (0.0052 mole) of 50% DCC in the same solvent was added. Shaking was continued for 90 minutes at which time a ninhydrin test was slightly positive. The coupling was repeated with 0.69 g. (0.0026 mole) of BOC-L-phenylalanine and 1.16 ml. (0.0026 mole) of 50% DCC in methylene chloride. A second ninhydrin test was negative indicating that the reaction was complete. Deprotection was accomplished by shaking for 10 minutes with 40 ml. of 25% TFA in methylene chloride, followed by 50 ml. of 50% TFA in methylene chloride for 30 minutes. The TFA solution was removed by filtration and the resin was washed twice each for 1 minute with 30 ml. volumes of methylene chloride, methanol and methylene chloride. The resin was dried to yield 6.28 g. of L-phenylalanine BHA resin. Titration by the Dorman method gave a value of 0.42 milliequivalents of free amine per gram of dry resin.

Cycle 38

A 4.76 g. (0.002 mole) quantity of resin peptide from Cycle 39, Example 8 was resuspended in 40 ml. of methylene chloride and 1.35 g. (0.004 mole) of BOC-L-glutamic acid γ-benzyl ester was added. After 10 minutes of mixing, 1.8 ml. (0.004 mole) of 50% DCC in methylene chloride was added. After 2 hours of mixing, the resin was washed twice for 1 minute each with 30 ml. of methylene chloride. A ninhydrin test indicated that the reaction was complete. A 30 ml. volume of 50% TFA in methylene chloride was added to deprotect the resin. After 30 minutes of mixing, the resin was filtered and washed twice each for 1 minute with methylene chloride, methanol and methylene chloride. After neutralization with two 5 minute reactions with 30 ml. of 10% triethylamine in methylene chloride, the resin was washed twice with 30 ml. volumes of methylene chloride for 1 minute.

Cycles 37-26

In each of these cycles, the coupling and deprotection procedures described in Cycle 38, Example 2 were repeated with 0.004 mole of the following amino acid derivatives in the order listed:

| Cycle No. | Wt., g. | Amino Acid Reactant |
|---|---|---|
| 37 | 0.96 | BOC-L-leucine hemidydrate |
| 36 | 0.86 | BOC-L-proline |
| 35 | 1.06 | BOC-L-phenylalanine |
| 34 | 0.76 | BOC-L-alanine |
| 33 | 1.35 | BOC-L-glutamic acid γ-benzyl ester |
| 32 | 0.76 | BOC-L-alanine |
| 31 | 1.18 | BOC-O-benzyl-L-serine |
| 30 | 1.35 | BOC-L-glutamic acid γ-benzyl ester |
| 29 | 1.29 | BOC-L-aspartic acid β-benzyl ester |
| 28 | 1.35 | BOC-L-glutamic acid γ-benzyl ester |
| 27 | 0.76 | BOC-L-alanine |
| 26 | 0.70 | BOC-glycine |

Cycle 25

To the resin peptide obtained from Cycle 26 was added 1.41 g. (0.004 mole) of BOC-L-asparagine p-nitrophenyl ester. After 16 hours of mixing, a negative ninhydrin test indicated that the reaction was complete. The resin peptide was deprotected with 30 ml. of 50% TFA in methylene chloride as in Cycle 38, Example 2.

Cycles 24-19

Continuing the synthesis with resin peptide from Cycle 25, the coupling and deprotection procedures described in Cycle 38, Example 2 was repeated with 0.004 mole of each of the amino acid derivatives in the order listed:

| Cycle No. | Wt., g. | Amino Acid Reactant |
|---|---|---|
| 24 | 0.86 | BOC-L-proline |
| 23 | 1.98 | BOC-O-(2-bromobenzyloxycarbonyl)-L-tyrosine |
| 22 | 0.87 | BOC-L-valine |
| 21 | 1.66 | BOC-ε-(2-chlorobenzyloxycarbonyl)-L-lysine |
| 20 | 0.87 | BOC-L-valine |
| 19 | 0.86 | BOC-L-proline |

Cycles 18-17

The coupling and deprotection procedures used in these cycles were the same as those described for Cycle 38, Example 2, except that the 0.004 mole of each of the amino acid derivatives was dissolved in a mixture of 5 ml. of dimethylformamide and 25 ml. of methylene chloride.

| Cycle No. | Wt., g. | Amino Acid Reactant |
|---|---|---|
| 18 | 1.70 | BOC-$N^g$-tosyl-L-arginine |
| 17 | 1.70 | BOC-$N^g$-tosyl-L-arginine |

Cycles 16-10

The coupling and deprotection procedures used in these cycles were the same as in Cycle 38, Example 2, except that 0.004 mole of the following amino acid derivatives was used:

| Cycle No. | Wt., g. | Amino Acid Reactant |
|---|---|---|
| 16 | 1.66 | BOC-ε-(2-chlorobenzyloxycarbonyl)-L-lysine |
| 15 | 1.66 | BOC-ε-(2-chlorobenzyloxycarbonyl)-L-lysine |
| 14 | 0.70 | BOC-glycine |
| 13 | 0.87 | BOC-L-valine |
| 12 | 0.86 | BOC-L-proline |
| 11 | 1.66 | BOC-ε-(2-chlorobenzyloxycarbonyl)-L-lysine |
| 10 | 0.70 | BOC-glycine |

Cycles 9-8

Same as Cycle 38, Example 2, except that 0.004 mole of each amino acid reactant was dissolved in a mixture of 5 ml. of dimethylformamide and 25 ml. of methylene chloride before addition to the resin peptide.

| Cycle No. | Wt., g. | Amino Acid Reactant |
|---|---|---|
| 9 | 1.22 | BOC-L-tryptophane |
| 8 | 1.70 | BOC-$N^6$-tosyl-L-arginine |

Cycles 7-2.

In each of the cycles listed below, 0.004 mole of the amino acid derivatives was coupled to the resin peptide and deprotected in the same manner as in Cycle 38, Example 2

| Cycle No. | Wt., g. | Amino Acid Reactant |
|---|---|---|
| 7 | 1.06 | BOC-L-phenylalanine |
| 6 | 1.55 | BOC-N-(im)-benzyloxycarbonyl-L-histidine |
| 5 | 1.35 | BOC-L-glutamic acid γ-benzyl ester |
| 4 | 1.00 | BOC-L-methionine |
| 3 | 1.18 | BOC-O-benzyl-L-serine |
| 2 | 1.98 | BOC-O-(2-brmobenzyloxycarbonyl)-L-tyrosine |

The resin peptide after Cycle 2 was dried in a vacuum oven at 50° C. overnight and weighed 13.45 g.

EXAMPLE 3

A 3.25 g. quantity of resin peptide from Cycle 2, Example 1 was washed for 1 minute with 25 ml. of methylene chloride. To the filtered resin was added 0.30 g. (0.001 mole) of BOC-O-benzyl-L-serine and 25 ml. of methylene chloride. After mixing for 10 minutes, 0.48 ml. (0.001 mole) of 50% DCC in methylene chloride was added. After mixing for 2 hours, a ninhydrin test indicated that the reaction was complete. The resin was deprotected in the same manner described in Cycle 39, Example 1 with 25 ml. of 50% TFA in methylene chloride. This resin peptide, when neutralized and dried, weighed 3.10 g.

EXAMPLE 4

A suspension of 0.48 g. (0.001 mole) of BOC-O-benzyl-D-serine dicyclohexylamine salt in 30 ml. of ethyl acetate was neutralized by washing with three 10 ml. volumes each 10% aqueous citric acid, water and saturated sodium chloride solution. The ethyl acetate layer was separated and distilled under vacuum at 40° C. The residue was dissolved in 30 ml of methylene chloride and the suspension was filtered. The filtrate was added to 3.26 g. of resin peptide from Cycle 2, Example 1. The coupling and deprotection steps were the same as Example 3. The dried resin peptide weighed 3.51 g.

EXAMPLE 5

Same as Example 3, except that 0.20 g. (0.001 mole) of BOC-L-alanine was used instead of BOC-O-benzyl-l-serine. The dried resin weighed 3.19 g.

EXAMPLE 6

Same as Example 3, except that 0.20 g. of BOC-D-alanine was used. The dried resin peptide weighed 3.07 g.

EXAMPLE 7

Same as Example 3, except that 0.20 g. of BOC-$\beta$-alanine was coupled to 3.25 g. of resin peptide similar to that obtained from Cycle 2, Example 1. The yield of finished resin peptide was 3.28 g.

EXAMPLE 8

Same as Example 3, except that 0.18 g. of BOC-glycine was coupled to 3.25 g. of resin peptide similar to that obtained from Cycle 2, Example 1. The yield of finished resin peptide was 3.19 g.

EXAMPLE 9

A 3.36 g. quantity of resin peptide from Cycle 2, Example 2, was washed for 1 minute with 25 ml. of methylene chloride. To the filtered resin was added 0.30 g. (0.001 mole) of BOC-O-benzyl-L-serine. After mixing for 10 minutes, 0.48 ml. (0.001 mole) of 50% DCC in methylene chloride was added. After 2 hours of additional mixing, a ninhydrin test indicated that the reaction was complete. The resin was deprotected in the same manner described in Cycle 38, Example 2 with 50% TFA in methylene chloride. The finished peptide weighed 3.24 g.

EXAMPLE 10

Same as Example 9, except that 0.30 (0.001 mole) of BOC-O-benzyl-D-serine was used. The dried resin peptide weighed 3.59 g.

EXAMPLE 11

Same as Example 9, except that 0.20 g. (0.001 mole) of BOC-L-alanine was used and 3.21 g. of dried resin peptide was obtained.

EXAMPLE 12

Same as Example 9 using 3.28 g. of resin peptide similar to that in Cycle 2, Example 2 and 0.20 g. (0.001 mole) of BOC-$\beta$-alanine. The yield of dried resin peptide was 3.33 g.

EXAMPLE 13

Same as Example 9, except that 0.20 g. (0.001 mole) of BOC-D-alanine was coupled to 3.37 g. of resin peptide from Cycle 2 in Example 2. The yield of finished resin peptide was 3.18 g.

EXAMPLE 14

Same as Example 9, except that 0.18 g. (0.001 mole) of BOC-glycine was coupled to 3.35 g. of resin peptide similar to that obtained from Cycle 2 in Example 2. The dried resin peptide weighed 3.28 g.

EXAMPLE 15

A 2.00 g. sample of dried resin peptide from Example 6 and 2 ml. of anisole were placed in a Teflon reaction vessel. The vessel, which was equipped with a Teflon-coated magnetic stirring bar, was placed in a Dry Ice-acetone bath and 15 ml. of hydrogen fluoride gas was condensed into the vessel. This mixture was stirred at 0° C. in an ice-bath for 1 hour. The hydrogen fluoride was removed by distillation at reduced pressure at room temperature. The residue was triturated with 40 ml. of ethyl acetate, and the solids were collected in a Buchner funnel. The solids were washed five more times with 40 ml. volumes of ethyl acetate. The peptide was extracted by percolating 30 ml. of 0.1 Molar acetic acid through the filter over a 10 minute period. The lumps were broken up with a glass stirring rod. The acetic acid extraction was repeated 3 times. The combined acetic acid extracts were frozen and lyophilized to yield 0.82 g. of crude [d-ala$^1$]-ACTH-(1-39)-amide.

EXAMPLE 16

A solution was prepared from 203.2 mg. of crude [d-ala$^1$]-ACTH-(1-39)-amide, obtained from the hydrogen fluoride treatment of 2.00 g. of the resin peptide from Example 6, and 1.2 g. of urea in 20 ml. of ammonium acetate buffer (pH 4, conductivity 4.0 millimhos at 25° C.). The solution was filtered and placed on a carboxymethyl cellulose column (CM52, bed volume 3.5 ml.). It was then chromatographed with 125 ml. of ammonium acetate buffer (pH6.5, conductivity 4.0 millimhos at 25° C.), followed by 50 ml. of a second ammonium acetate buffer (pH6.9, conductivity 16.0 millimhos at 25° C.). The major peak fractions, determined by reading the optical density at 280 nanometers wavelength using an ultraviolet absorptiometer, were collected and lyophilized. The lyophilized material was dissolved in 5 ml. of 0.5 N acetic acid and desalted by gel filtration through a Sephadex G-25 column (fine mesh, bed volume 100 ml.). Again, the major peak fractions, determined by ultraviolet absorption at 280 nanometers wavelength, were pooled and lyophilized. The yield was 52.5 mg. of purified [d-ala$^1$]-ACTH-(1-39)-amide.

While we have set forth in detail certain embodiments of our invention, it is to be understood that many changes may be made all within the spirit of the invention and the scope of the appended claims.

We claim:

1. A resin peptide having the structure:

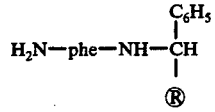

wherein ® is divinylbenzene crosslinked polystyrene.

2. A resin peptide having the structure:

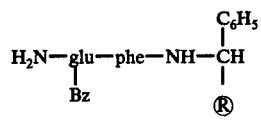

wherein ® is divinylbenzene crosslinked polystyrene and Bz is benzyl, p-methoxybenzyl, p-chlorobenzyl, p-nitrobenzyl or benzylhydryl.

3. A resin peptide having the structure:

$$\text{H}_2\text{N-ser-ala-glu-ala-phe-pro-leu-glu-phe-NH-CH}\begin{array}{c}\text{C}_6\text{H}_5\\|\\\end{array}$$
with Bz on ser, ala(?), phe and ®

H₂N-ser-ala-glu-ala-phe-pro-leu-glu-phe-NH-CH(C₆H₅)-®
        |                       |
        Bz                      Bz
with Bz groups on ser and leu positions wherein ® is divinylbenzene crosslinked polystyrene and Bz is benzyl, p-methoxybenzyl, p-chlorobenzyl, p-nitrobenzyl or benzylhydryl.

4. A resin peptide having the following structure:

H₂N—asp—ala—gly—glu—asp—gln—ser—ala—
     |         |    |    |
     Bz        Bz   Bz   Bz glu—ala—phe—pro—leu—glu—phe—NH—CH(C₆H₅)—®
 |                   |
 Bz                  Bz wherein ® is divinylbenzene crosslinked polystyrene and Bz is benzyl, p-methoxybenzyl, p-chlorobenzyl, p-nitrobenzyl or benzylhydryl.

5. A resin peptide having the following structure:

H₂N—X-tyr-ser-met-glu-his-phe-arg-trp-gly-
     |   |       |       |
     Y   Bz      Bz      W   T(?)

lys-pro-val-gly-lys-lys-arg-arg-pro-val-lys-
 |           |   |   |           |
 V           V   V   T   T       V val-tyr-pro-asp-ala-gly-glu-asp-gln-ser-ala-
 |           |       |   |   |
 Y           Bz      Bz  Bz  Bz glu-ala-phe-pro-leu-glu-phe-NH—CH(C₆H₅)—®
 |                   |
 Bz                  Bz where ® is divinylbenzene crosslinked polystyrene and Bz is benzyl, p-methoxybenzyl, p-chlorobenzyl, p-nitrobenzyl or benzylhydryl and Y is H, Bz, benzyloxycarbonyl, 2-chlorobenzyloxycarbonyl, 2-bromobenzyloxycarbonyl, X is l-ser, D-ser,
 |      |
 Bz     Bz L-ala, D-ala, β-ala or gly, V is 2-chlorobenzyloxycarbonyl, benzyloxycarbonyl, 2-bromobenzyloxycarbonyl or 2,4-dichloorobenzyloxycarbonyl, T is nitro or tosyl and W is H benzyloxycarbonyl, tosyl, dinitrophenyl or benzyl.

6. A resin peptide as set forth in claim 5 wherein X is

L-ser.
 |
 Bz

7. A resin peptide as set forth in claim 5 wherein X is

D-ser.
 |
 Bz

8. A resin peptide as set forth in claim 5 in which X is L-ala.

9. A resin peptide as set forth in claim 5 in which X is gly.

10. A resin peptide having the structure:

H₂N-asn-gly-ala-glu-asp-glu-ser-ala-glu-ala-
         |   |       |           |
         Bz  Bz      Bz          Bz phe-pro-leu-glu-phe-NH—CH(C₆H₅)—®
             |
             Bz in which Bz is benzyl, p-methoxybenzyl, p-chlorobenzyl, p-nitrobenzyl or benzylhydryl and ® is divinylbenzene crosslinked polystyrene.

11. A resin peptide having the structure:

H₂N-glu-ser-ala-glu-ala-phe-pro-leu-glu-phe-NH—CH(C₆H₅)—®
     |                           |
     Bz                          Bz in which Bz is benzyl, p-methoxybenzyl, p-chlorobenzyl, p-nitrobenzyl or benzylhydryl and ® is divinylbenzene cross-linked polystyrene.

12. A resin peptide having the structure:

H₂N-X-tyr-ser-met-glu-his-phe-arg-trp-gly
     |   |       |       |
     Y   Bz      Bz      W   T lys-pro-val-gly-lys-lys-arg-arg-pro-val-lys
 |           |   |   |           |
 V           V   V   T   T       V val-tyr-pro-asn-gly-ala-glu-asp-glu-ser-ala-
 |                   |       |   |
 Y                   Bz      Bz  Bz glu-ala-phe-pro-leu-glu-phe-NH-CH(C₆H₅)—®
 |                   |
 Bz                  Bz in which Bz is benzyl, p-methoxybenzyl, p-chlorobenzyl, p-nitrobenzyl or benzylhydryl Y is H, Bz, benzyloxycarbonyl, 2-chlorobenzyloxycarbonyl or 2-bromobenzyloxycarbonyl.

V is 2-chlorocarbobenzyloxy, benzyloxycarbonyl, 2-bromocarbobenzyloxy, or 2,4-dichlorocarbobenzyloxy, ® is divinylbenzene crosslinked polystyrene, T is nitro or tosyl and X is L-serine, D-serine,
 |         |
 Bz        Bz L-alanine, D-alanine, β-alanine, or glycine.

13. A resin peptide as set forth in claim 12 in which X is L-serine.

14. A resin peptide as set forth in claim 12 in which X is D-serine.

15. A resin peptide as set forth in claim 12 in which X is L-alanine.

16. A resin peptide as set forth in claim 12 in which X is β-alanine.

17. A resin peptide as set forth in claim 12 in which X is glycine.

18. A peptide having the following structure:

H₂N-X-tyr-ser-met-glu-his-phe-arg-trp-gly-lys-pro-val-gly-lys-lys-arg-arg-pro-val-lys-val-tyr-pro-asp-ala-gly-glu-asp-gln-ser-ala-glu-ala-phe-pro-leu-glu-phe where X is L-ser, D-ser, L-ala, D-ala, β-ala or gly, and wherein the terminal phe is an amide.

19. A peptide as set forth in claim 18 in which X is L-ser.

20. A peptide as set forth in claim 18 in which X is D-ser.

21. A peptide as set forth in claim 18 in which X is D-ala.

22. A peptide having the following structure:

H₂N-X-tyr-ser-met-glu-his-phe-arg-trp-gly-lys-pro-val-gly-lys-lys-arg-arg-pro-val-lys-val-tyr-pro-asn-gly-ala-glu-asp-glu-ser-ala-glu-ala-phe-pro-leu-glu-phe where X is L-ser, D-ser, L-ala, D-ala, β-ala or gly, and wherein the terminal phe is an amide.

23. A peptide as set forth in claim 22 in which X is L-ser.

24. A peptide as set forth in claim 22 in which X is D-ser.

25. A peptide as set forth in claim 22 in which X is D-ala.

* * * * *